(12) United States Patent
Hechler et al.

(10) Patent No.: US 7,214,821 B2
(45) Date of Patent: May 8, 2007

(54) PREPARATION OF (METH)ACROLEIN AND/OR (METH)ACRYLIC ACID BY HETEROGENEOUSLY CATALYZED PARTIAL OXIDATION OF $C_3$ AND/OR $C_4$ PRECURSOR COMPOUNDS

(75) Inventors: Claus Hechler, Ludwigshafen (DE); Gerhard Olbert, Dossenheim (DE); Dietmar Loewen, Thaleischweiler-Froeschen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 319 days.

(21) Appl. No.: 11/019,160

(22) Filed: Dec. 23, 2004

(65) Prior Publication Data

US 2005/0159618 A1 Jul. 21, 2005

Related U.S. Application Data

(60) Provisional application No. 60/531,677, filed on Dec. 23, 2003.

(30) Foreign Application Priority Data

Dec. 23, 2003 (DE) .............................. 103 61 456

(51) Int. Cl.
*C07C 229/00* (2006.01)

(52) U.S. Cl. ...................................... 562/532; 562/600

(58) Field of Classification Search ................. 562/532
See application file for complete search history.

(56) References Cited

FOREIGN PATENT DOCUMENTS

DE      10110847 A1 *  9/2002

* cited by examiner

*Primary Examiner*—Samuel Barts
*Assistant Examiner*—Sudhakar Katakam
(74) *Attorney, Agent, or Firm*—Oblon, Spivak, McClelland, Maier & Neustadt, P.C.

(57) ABSTRACT

A process is proposed for preparing (meth)acrolein and/or (meth)acrylic acid by partially oxidizing $C_3$ and/or $C_4$ precursor compounds in the gas phase in the presence of a heterogeneous particulate catalyst, in a reactor having two or more thermoplates (1) arranged vertically and parallel to each other while in each case leaving a gap (2), the heterogeneous particulate catalyst being installed in the gaps (2) and the gaseous reaction mixture being passed through the gaps (2), which comprises monitoring, controlling and/or regulating the process by selecting as a monitoring, control and/or regulation parameter one or more temperatures which are measured in one or more gaps (2), at one or more measurement points which are distributed over the height of each gap (2).

28 Claims, 10 Drawing Sheets

Figure 1:
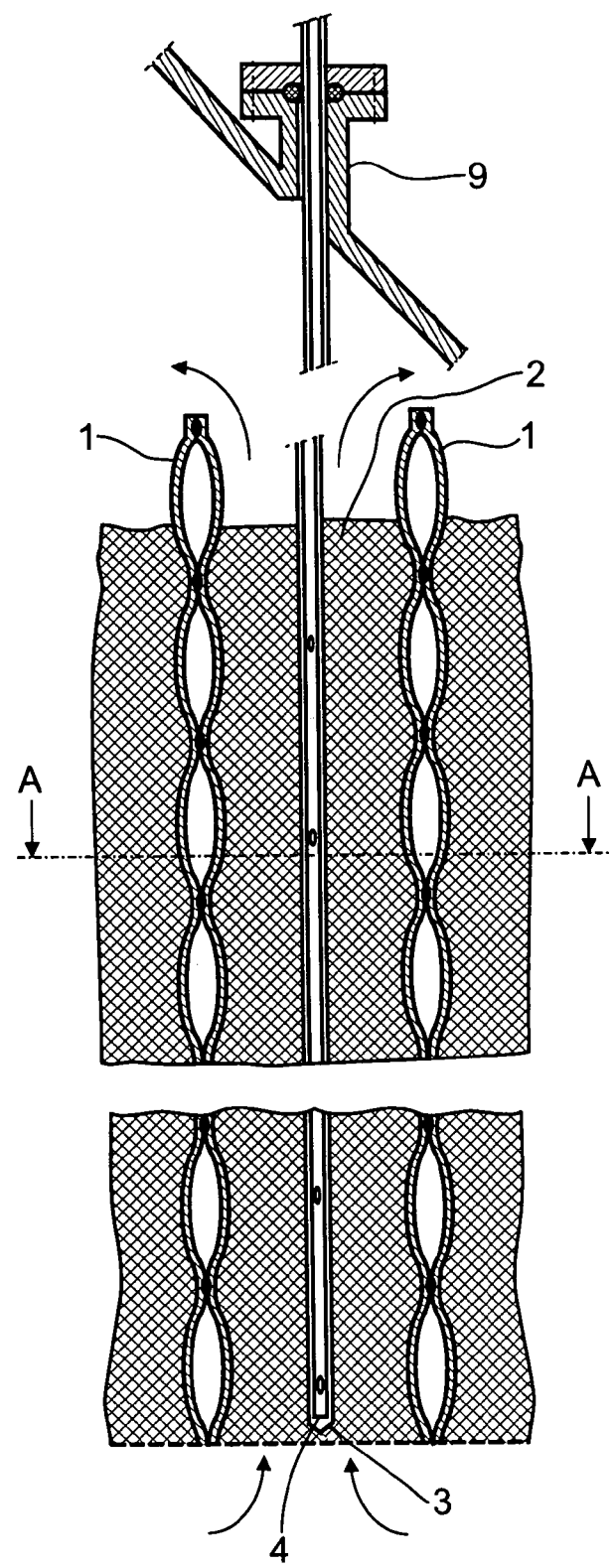

PREPARATION OF (METH)ACROLEIN AND/OR (METH)ACRYLIC ACID BY HETEROGENEOUSLY CATALYZED PARTIAL OXIDATION OF $C_3$ AND/OR $C_4$ PRECURSOR COMPOUNDS

The invention relates to a process for preparing (meth)acrolein and/or (meth)acrylic acid by partial oxidation in the gas phase of $C_3$ and/or $C_4$ precursor compounds in the presence of a heterogeneous particulate catalyst in 1, 2 or 3 reaction stages in a reactor having thermoplate modules.

As is well known, the abbreviated notation (meth)acrolein denotes acrolein and/or methacrolein. In a similar manner, the abbreviated notation (meth)acrylic acid is used for acrylic acid and/or methacrylic acid.

As is well known, the partial oxidation of $C_3$ and/or $C_4$ precursor compounds, such as propylene, propane, isobutene, isobutane, isobutanol, the methyl ether of isobutanol, acrolein or methacrolein (i.e. in particular of hydrocarbons containing 3 or 4 carbon atoms) in the gas phase is carried out in the presence of heterogeneous particulate catalysts. These reactions are strongly exothermic and have hitherto been carried out on the industrial scale predominantly in tube bundle reactors having catalyst tubes, into which the heterogeneous particulate catalyst is introduced and through which the gaseous reaction mixture is passed, and the heat of reaction which is released is removed indirectly via a heat carrier which circulates in the intermediate space between the catalyst tubes. The heat carrier used is frequently a salt melt.

The reaction can be carried out starting from an alkane in one reaction stage to the acid, or in a first stage to the aldehyde and in a second stage to the acid. An alternative procedure may go in a first of three stages from the alkane to the olefin, in a second from the olefin to the aldehyde and in a third from the aldehyde to the acid. Starting from the olefin, the oxidation may in turn be effected in two stages, first to the aldehyde and then to the acid, or else in one stage from the olefin to the acid. The acid may also be prepared in one stage starting from the particular aldehyde. In this context, the aldehyde is (meth)acrolein and the acid is (meth)acrylic acid.

As an alternative, it is also possible to remove the heat of reaction via a heat carrier which is passed through plate-type heat transferrers. The terms heat exchanger plates, heat transferrer plates and thermoplates are used substantially synonymously for plate-type heat transferrers.

Heat transferrer plates are defined as predominantly sheetlike structures which have an interior provided with inlet and outlet lines and having a low thickness in comparison to the surface area. They are generally produced from metal sheets, frequently from steel sheets. However, depending on the application case, in particular on the properties of the reaction medium and of the heat carrier, special, in particular corrosion-resistant, or else coated materials may be used. The inlet and outlet devices for the heat carriers are generally arranged at opposite ends of the heat exchanger plates. The heat carriers used are frequently water, or else Diphyl® (mixture of from 70 to 75% by weight of diphenyl ether and from 25 to 30% by weight of diphenyl), which sometimes also evaporate in a boiling operation; it is also possible to use other organic heat carriers having a low vapor pressure and also ionic liquids.

The use of ionic liquids as heat carriers is described in the German patent application DE 103 16 418. Preference is given to ionic liquids which contain a sulfate, phosphate, borate or silicate anion. Also particularly suitable are ionic liquids which contain a monovalent metal cation, in particular an alkali metal cation, and also a further cation, in particular an imidazolium cation. Also advantageous are ionic liquids which contain an imidazolium, pyridinium or phosphonium cation as the cation.

The term thermoplates is used in particular for heat transferrer plates whose single, usually two, metal plates are joined together by point and/or roll welds and are frequently shaped using hydraulic pressure plastically to form pockets.

In the present context, the terms heat exchanger plates, heat transferrer plates and thermoplates are used in the sense of the above definition.

Reactors for carrying out partial oxidations using thermoplates are known, for example, from DE-A 199 52 964. The arrangement is described of a catalyst for carrying out partial oxidations in a bed around heat transferrer plates in a reactor. The reaction mixture is fed at one reactor end to the reactor interior between the heat transferrer plates and removed at the opposite end and thus flows through the interior between the heat transferrer plates.

DE-C 197 54 185 describes a further reactor having indirect heat removal via a cooling medium which flows through heat transferrer plates, the heat transferrer plates being designed as thermoplates which consist of at least two steel plates which are joined together at predefined points to form flow channels.

An advantageous development thereof is described in DE-A 198 48 208, according to which heat transferrer plates which are configured as thermal plates flowed through by a cooling medium are combined to give plate assemblies having, for example, rectangular or square cross section, and the plate assemblies have a casing. The encased plate assembly needs no adaptation on the circumferential side and is consequently used with predefined spacings to the interior wall of the cylindrical reactor vessel. The free surfaces between the plate heat transferrer or its casing and the vessel interior wall are covered in the upper and lower regions of the casing with guide plates, in order to prevent the reaction medium from bypassing the chambers filled with catalyst.

A further reactor having devices for removing the heat of reaction which are in the form of plate heat transferrers is described in WO-A 01/85331. The reactor of predominantly cylindrical shape contains a continuous catalyst bed, into which a plate heat transferrer is embedded.

DE-A 103 33 866 discloses the prevention of problems which occur as a result of deformations which are a consequence of high stress on one side of the thermoplates in the event of an excessively high pressure differential between the reaction mixture and the external environment, and also mechanical stability problems as a result of reshaping under high thermal stress, which can occur when the reaction mixture is under elevated pressure or reduced pressure, by providing a reactor for partial oxidations of a fluid reaction mixture in the presence of a heterogeneous particulate catalyst, having one or more cuboidal thermoplate modules which are each formed from two or more rectangular thermoplates arranged parallel to each other while in each case leaving a gap which can be filled with the heterogeneous particulate catalyst and is flowed through by the fluid reaction mixture, the heat of reaction being absorbed by a heat carrier which flows through the thermoplates and thus at least partly evaporating, having a predominantly cylindrical shell which releases the pressure at the thermoplate modules, completely surrounds them and comprises a cylinder jacket and hoods which close it at both ends and whose longitudinal axis is aligned parallel to the plane of the thermoplates, and also having one or more sealing elements which are arranged in such a way that the gaseous reaction mixture, apart from flowing through the reactor interiors bounded by the hoods, only flows through the gaps.

It is accordingly an object of the invention to provide a process for monitoring, control and/or regulation in a process for preparing (meth)acrolein and/or (meth)acrylic acid by partial oxidation of $C_3$ and/or $C_4$ precursor compounds in the gas phase.

Accordingly a process has been found for preparing (meth)acrolein and/or (meth)acrylic acid by partially oxidizing $C_3$ and/or $C_4$ precursor compounds in the gas phase in the presence of a heterogeneous particulate catalyst, in a reactor having two or more thermoplates 1 arranged vertically and parallel to each other while in each case leaving a gap 2, the heterogeneous particulate catalyst being installed in the gaps 2 and the gaseous reaction mixture being passed through the gaps 2, which comprises monitoring, controlling and/or regulating the process by selecting as a monitoring, control and/or regulation parameter one or more temperatures which are measured in one or more gaps 2, at one or more measurement points which are distributed over the height of each gap 2.

Preferably, the composition of the fluid reaction mixture in one or more gaps is additionally selected as a further monitoring, control and/or regulation parameter and is determined at one or more measurement points which are distributed over the height of each gap.

For the determination of the operating conditions of reactors, the knowledge of the temperature field in the catalyst bed is of substantial importance. This relates to the local distribution of the temperature, and also, for example, the magnitude and position of the temperature maximum (hotspot). The temperature profile along the flow path of the reaction medium may also be important for the control and regulation of the reaction system.

In addition to the steady-state operation, the startup or shutdown or, for instance, boundary conditions of operation which vary with time even over prolonged periods, for example a change in the catalyst activity (deactivation) also have to be controlled. On the basis of measured temperatures, it is possible, for example, to ensure safe operation, but also to control and maintain the optimum operating state which is preferred in each case. Conclusions are possible on the favorable operating mode, for example with regard to reactant composition and reactant flow rate, but also cooling temperature and cooling medium throughput. Moreover, additional concentration measurement in the catalyst bed allows the substance profile of the reaction to be monitored and, for example, the reaction kinetics also to be determined under operating conditions. For example, the deactivation behavior of the catalyst can also be characterized with reference to concentration profiles in the course of flowthrough, especially together with temperature profiles, which can also be utilized for advantageous reaction control with low by-product formation by adapting to the gas load, or else for improvement of the catalyst and of the reactor design.

According to the prior art, it is necessary in the case of tube bundle reactors, when temperature measurement sleeves or temperature measurement inserts are inserted into the catalyst bed, to use specially manufactured tubes having increased internal diameter in order to enable an equivalent reaction profile to the remaining, normal reaction tubes in these tubes, and thus a representative temperature measurement.

The inventors have recognized that it is possible to determine the temperature profile in the particulate catalyst which has been introduced into the gap between two thermoplates over the height thereof, i.e. the temperature profile along the flow path, and also the concentration profile over the height of the catalyst, i.e. the concentration profile along the flow path, without disturbing the process by the measurement operation itself.

Reactors having thermoplates have already been described above.

The thermoplates are manufactured from preferably corrosion-free materials, especially from stainless steel, for example having the materials number 1.4541 or 1.4404, 1.4571 or 1.4406, 1.4539 or else 1.4547 and 1.4301, or from other alloyed steels.

The material thickness of the metal sheets used for this purpose may be selected between 1 and 4 mm, 1.5 and 3 mm, or else between 2 and 2.5 mm, or at 2.5 mm.

In general, two rectangular metal sheets may be joined at the longitudinal and end sides to give a thermoplate, in which case a roll seam or lateral weld joint or a combination of both is possible so that the space in which the heat carrier is later disposed is sealed on all sides. The edge of the thermoplates is advantageously removed at or even in the lateral roll seam of the longitudinal edge so that the edge region, which is poorly cooled if at all, and in which catalyst has usually also been installed, has a very low geometric expansion.

The metal sheets are joined together by point welding distributed over the rectangular surface. An at least partial connection by straight or else curved and also circular roll seams is also possible. It is also possible for the volume flowed through by the heat carrier to be divided by additional roll seams into a plurality of separate regions.

One possibility of arranging the weld points on the thermoplates is in rows with equidistant point separations of from 30 to 80 mm or else from 35 to 70 mm, although separations of 40 to 60 mm are also possible and a further embodiment has separations of from 45 to 50 mm and also from 46 to 48 mm. Typically, as a result of the manufacture, the point separations vary by up to ±1 mm and the weld points of immediately adjacent rows, viewed in the longitudinal direction of the plates, are each arranged offset by half a weld point separation. The rows of the point welds in the longitudinal direction of the plates may be equidistant with separations of from 5 to 50 mm, or else from 8 to 25 mm, although separations of from 10 to 20 mm and also from 12 to 14 mm, may also be used. Moreover, pairings of the weld point separations and row separations mentioned which are adapted to the application case are also possible. The row separations may be in a defined geometric relationship to the point separation, typically ¼ of the point separations or somewhat lower, so that there is a defined uniform expansion of the thermoplates in the course of the production. For predefined weld point and row separations, a corresponding number of weld points per $m^2$ of plate surface area is designated; possible values are from 200 to 3000, typical values from 1400 to 2600, weld points per $m^2$ of the plate surface. Advantageously, from 20 to 35 weld points lie within a rectangular surface section of 5×weld point separation by 5×row separation.

The width of the thermoplates is limited substantially by manufacturing technology considerations and may be between 100 and 2500 mm, or else between 500 and 1500 mm. The length of the thermoplates is dependent upon the reaction, in particular upon the temperature profile of the reaction, and may be between 500 and 7000 mm, or else between 3000 and 4000 mm.

In each case two or more thermoplates are arranged parallel and separated from one another to form a thermoplate module. This results in shaftlike gaps forming between immediately adjacent plates which, at the narrowest points of the plate separation, for example, have a width of between 8 and 150 mm, or else from 10 to 100 mm. One possible embodiment is also widths of from 12 to 50 mm or else from 14 to 25 mm, although from 16 to 20 mm may also be selected. A gap separation of 17 mm has also been tested.

Between the individual thermoplates of a thermoplate module, for example in the case of large-surface-area plates, spacers can additionally be installed in order to prevent deformations which can change plate separation or position. To install these spacers, sections of the metal plates can be removed from the flow region of the heat carrier, for example by circular roll seams or weld points of greater diameter, in order, for example, to be able to introduce holes into the plates in the middle of the sections for rod-shaped spacers which may be secured by screws or welds.

The gaps between the individual plates may have the same separation, but, if required, the gaps may also be of different width when the reaction permits it or the desired reaction requires it, or apparatus or cooling technology advantages can be achieved.

The gaps of a thermoplate module filled with catalyst particles may be sealed with respect to each other, for example sealed by welding, or else be joined together on the process side.

To adjust the desired gap separation when joining the individual thermoplates together to form a module, the plates are secured in their position and in separation.

The weld points of immediately adjacent thermoplates may be opposite each other or offset from each other.

The invention also provides an apparatus for carrying out the above-described process, characterized by a sleeve which is disposed in the gap between two thermoplates, preferably in longitudinal direction, and opens outside the reactor and which encloses a temperature measurement insert, for example one or more thermoelements having one or more measurement points.

The thermoplates are preferably disposed in
one or more cuboidal thermoplate modules which are each formed from two or more rectangular thermoplates arranged parallel to each other while in each case leaving a gap,
the thermoplate modules are completely surrounded by a pressure-releasing, predominantly cylindrical shell, comprising a cylinder jacket and hoods which close it at both ends and whose longitudinal axis is aligned parallel to the plane of the thermoplates,
one or more sealing elements are arranged in such a way that the gaseous reaction mixture, apart from flowing through the reactor interiors bounded by the hoods, only flows through the gaps, and
each thermoplate module having one or more mutually independent temperature measurement inserts is equipped preferably with two or three, more preferably with three, temperature measurement inserts.

By virtue of each thermoplate module being equipped with in each case at least one independent temperature measurement insert, each thermoplate module may be individually assessed and monitored. It is advantageous to provide more than one temperature measurement insert for each thermoplate module so that, in the event of failure of an individual temperature measurement insert, safe operation is nevertheless ensured. When in each case three temperature measurement inserts are used per thermoplate module, it is possible to maintain safe operation in the event of testing, maintenance or failure of a temperature measurement insert, especially when the temperature signals are utilized functionally in a protective circuit.

The sleeve is a preferably metallic tube, especially having an external diameter in the range from 4 to 15 mm, especially from 6 to 10 mm, frequently from 6 to 8 mm, and further preferably having a wall thickness of from 0.8 to 1.5 mm, preferably of 1 mm. Useful materials for the sleeve are in principle the same materials which can be used for the thermoplates, although sleeve and thermoplates do not have to be made of the same material. Nonferrous materials may also be used as the sleeve.

According to the prior art, it is necessary in the case of tube bundle reactors, when temperature measurement sleeves or temperature measurement inserts are inserted into the catalyst bed, to use specially manufactured tubes having increased internal diameter in order to enable an equivalent reaction profile to the remaining, normal reaction tubes in these tubes, and thus a representative temperature measurement.

While the customary arrangement of sleeves for accommodating measuring elements in reaction tubes, centrally, in the longitudinal axis thereof, results in high distortion of the flow and temperature profile compared to reaction tubes without installed sleeves, and therefore necessitates special configurations of the reaction tube, of the catalyst charge and also of the sleeve, for example with different wall thickness over its cross section, or special arrangements of the sleeve in the catalyst tube, as described in DE-A 101 10 847, it has been found that, surprisingly, reactors having thermoplates do not necessarily require such specific arrangements in the gaps between the thermoplates to measure the temperature profile in the catalyst bed.

It is necessary merely to dispose the temperature measurement insert itself or the sleeve which encloses the temperature measurement insert in the gap, preferably in the longitudinal direction between two thermoplates.

The distance of the temperature measurement insert or of the sleeve from the two thermoplates may preferably in each case be equal, i.e., in one embodiment, the temperature measurement insert is disposed centrally in the gap.

To introduce the sleeve into the gap between the thermoplates, it is particularly advantageous when the thermoplates each have the same weld point pattern and the weld points of adjacent thermoplates are opposite each other.

The sleeves may open outside the reactor both above and below it. In a preferred embodiment, it is possible that the sleeves open both above and below the reactor. In this case, the temperature measurement insert may be shifted continuously in the sleeve, so that a continuous illustration of the temperature profile can be determined, not only discrete temperature measurements. For this purpose, an individual measuring element, but advantageously also a multiple measuring element, particularly advantageously having equidistant measurement separations may be used, since the necessary shifting length for uninterrupted measurement of the temperature profile is then only one measurement point separation.

The sleeves may be conducted seamlessly through the outer reactor jacket or else have connecting elements in the region above the catalyst-charged thermoplate modules, or, in the case of introduction from below, below the thermoplate modules. In a particularly advantageous variant, the sleeves are provided with disconnection points in the reactor interior which are designed in particular as a cutting-ring or clamp-ring connection, so that the assembly is made considerably easier.

The temperature measurement insert generally has a plurality of measurement points distributed over its length and thus over the height of the gap. Useful temperature measurement inserts are preferably multiple measurement inserts (known as multi thermoelements), although all other, especially physical, temperature measurement principles such as platinum resistance thermometers, for example PT-100 or PT-1000, resistance thermometers or semiconductor sensors may also be used. Depending on the use temperature, useful thermoelements are all of those described in DIN43710 and DIN EN 60584, preferably K-type thermoelements according to DIN EN 60584.

The distributed measurement points may be arranged equidistantly, but particularly advantageously are arranged with a relatively small separation from each other in reactor regions having expected temperature extremes and/or particularly large temperature gradients, and with a relatively large separation from each other in the remaining reactor regions.

The temperature measurement insert advantageously has from 5 to 60 measurement points, preferably from 10 to 50 measurement points, more preferably from 15 to 40 measurement points and still more preferably from 20 to 30 measurement points.

In a preferred embodiment, the temperature measurement insert has 20 measurement points and an external diameter of about 3.8 mm, so that the temperature measurement insert can be installed in a sleeve having an external diameter of 6 mm or of ¼ inch and an internal diameter of 4 mm or of 5/32 inch.

In a further preferred embodiment, the temperature measurement insert has 40 measurement points and an external diameter of about 2.5 mm, so that the temperature measurement insert can be installed in a sleeve having an external diameter of 5 mm or of 3/16 inch and an internal diameter of 3 mm or of ⅛ inch.

In one embodiment, the sleeve which encloses the thermoelement may be disposed at the lateral boundary of the gap between two thermoplates. In order to prevent measurement distortion, preference is given in this case to providing an insulation element between the lateral boundary of the gap and the sleeve, so that a representative temperature signal can also be obtained at the edge of the bed. It is particularly advantageous in this case that the sleeve has been installed in the gap in a fixed manner and can remain there and does not have to be installed and removed together with the catalyst charge. In this case, the sleeve may also be designed with noncylindrical geometry, for example with a square or semicircular cross section.

In addition, it is also possible to dispose the sleeve which encloses the thermoelement horizontally in the gap between two thermoplates. This allows the temperature profile to be determined over the cross section of the gap.

In a further preferred embodiment of the inventive apparatus, in addition to the above-described sleeve having temperature measurement, in each case one sleeve is provided in one or more gaps and has perforations and also at least one sampling tube for introduction into the interior of the sleeve, said sampling tube being disposed there in such a way that the gaseous reaction mixture flows through the perforations in the sleeve into the interior of the sampling tube and is removed from the sampling tube after outside the reactor and analyzed.

The sleeve used is generally a metallic tube, preferably having an external diameter in the range from 5 to 15 mm, in particular from 8 to 10 mm, and a wall thickness of preferably 1 mm. According to the invention, the sleeve has perforations, i.e. orifices toward the reaction space, which are in principle not restricted with regard to their geometric shape. However, preference is given to the orifices having a circular shape. In particular, a slotlike shape with arrangement of the slots in the longitudinal direction of the sampling tube is also possible. The perforations preferably have a total surface area of from 1 to 50%, preferably of from 1 to 10%, of the total jacket surface area of the sleeve. They serve to allow the gaseous reaction mixture to flow into the sleeve, and thus get into the sampling tube disposed in the interior of the sleeve via the orifice thereof. The sample taken from the sampling tube outside the reactor may be analyzed, for example, with the available plant analytical instrumentation. It is equally possible to take samples and to analyze them continuously or at certain time intervals.

The withdrawal of the samples may be effected by the autogenous pressure of the reaction system through a control valve or overflow device, or else by means of a pump or compressor or of a radiator/ejector, and the sample may be introduced into a system having atmospheric pressure or else reduced or elevated pressure relative to the atmosphere. Preference is given to controlling the analytical system, into which the sample is introduced, at constant pressure to increase the measurement precision.

In a preferred embodiment, the perforated sleeve is disposed in the center of the gap. In this arrangement, the symmetry of the flow profile in the gap is disrupted to a particularly small extent. The installation may be vertically from above or below, and the installation is preferably from the same side of the reactor as the feed of the fluid reaction mixture.

In the embodiment in which both the installation of the sleeves and the feed of the fluid reaction mixture into the reactor are each from above, the sleeves are advantageously equipped with perforations only in the upper region of the gap, in particular up to about the middle thereof. Since the sampling tube extends only in the upper region of the sleeve up to the point at which the sample is taken through the orifice for the purpose of determining its composition, the empty region of the sleeve disposed below it would otherwise constitute a bypass for the reaction mixture. This is prevented by providing perforations in the sleeve only in the upper region of the gap.

Similarly, it is possible that the installation of the sleeves and the feed of the fluid reaction mixture into the reactor are each from below and that a heat carrier is preferably passed through the thermoplates and boiled partially or fully under reaction conditions.

The sampling tube may preferably be connected to the sleeve in a fixed manner, in such a way that the orifice of the sampling tube is disposed directly on a perforation of the sleeve, and the orifices of sampling tube and sleeve thus overlap.

In a further preferred embodiment, the sampling tube is disposed in the perforated sleeve in a rotatable manner and has at least two orifices disposed over its jacket surface offset in such a way that the gaseous reaction mixture always flows into the sampling tube only through one of the orifices. The orifices of the sampling tube are preferably disposed as slots in the longitudinal direction thereof, which makes available more room for manoeuver when matching the orifices of sleeve and sampling tube.

This embodiment allows samples to be taken from a plurality of points which are distributed over the height of the gap by means of a single sampling tube.

In a further preferred variant, each sampling tube has at least two, preferably from two to four, mutually separate chambers, each having an orifice into which the gaseous reaction mixture flows through the perforations of the sleeve, and the gaseous reaction mixture is removed separately from each chamber and analyzed. The chambers may be arranged mutually adjacently or concentrically.

The formation of two or more separate chambers in the sampling tubes increases the number of measurement points at which samples of the fluid reaction mixture can be taken.

Particular preference is given to the embodiment in which a sampling tube is provided with a plurality of chambers and is additionally disposed in a rotatable manner about its longitudinal axis. This allows two or more, preferably four, mutually offset slots for each chamber to be disposed for taking up the gaseous reaction mixture, in which case the gaseous reaction mixture flows into each chamber always in each case through only one orifice. This embodiment further increases the number of measurement points for the composition of the gaseous reaction mixture.

In a further preferred embodiment, two or more sampling tubes are provided and are each connected in a fixed manner to the sleeve, in such a way that the orifice of each sampling tube is disposed directly on a perforation of the sleeve, and the individual sampling tubes open in the gap each at a different height. Moreover, it is also possible to configure the sleeves themselves as sampling tubes by providing perforations only at those points at which there is a direct connection with in each case one sampling tube, and additionally providing a single further perforation in the sleeve at a different point to the opening of the sampling tube, through which the gaseous reaction mixture flows in.

The process according to the invention thus makes possible precise knowledge of the actual reaction events and the real temperatures, preferably also the temperature which is crucial for the hotspot, in a simple manner, utilizing available plant analytical instrumentation. This allows operation substantially closer to the load limit of the catalyst; the catalyst can thus be better utilized, and damage by undesirably high hotspot formation is at the same time prevented. In addition, with knowledge of the actual reaction events, the catalyst activity can be configured spatially in the gap in a varying manner, matched to the actual reaction events. This protects the catalyst, especially in the more thermally stressed regions, and thus increases its aging limit.

In addition, the reactor for preparing (meth)acrolein and/or (meth)acrylic acid can be operated substantially more uniformly, which allows the overall selectivity of the reactions taking place therein to be positively influenced. In addition, adaptation of the catalyst activity to the actual reaction events allows the required amount of heat carrier to be reduced.

The invention is illustrated in detail hereinbelow with reference to a drawing.

Figure 1A:
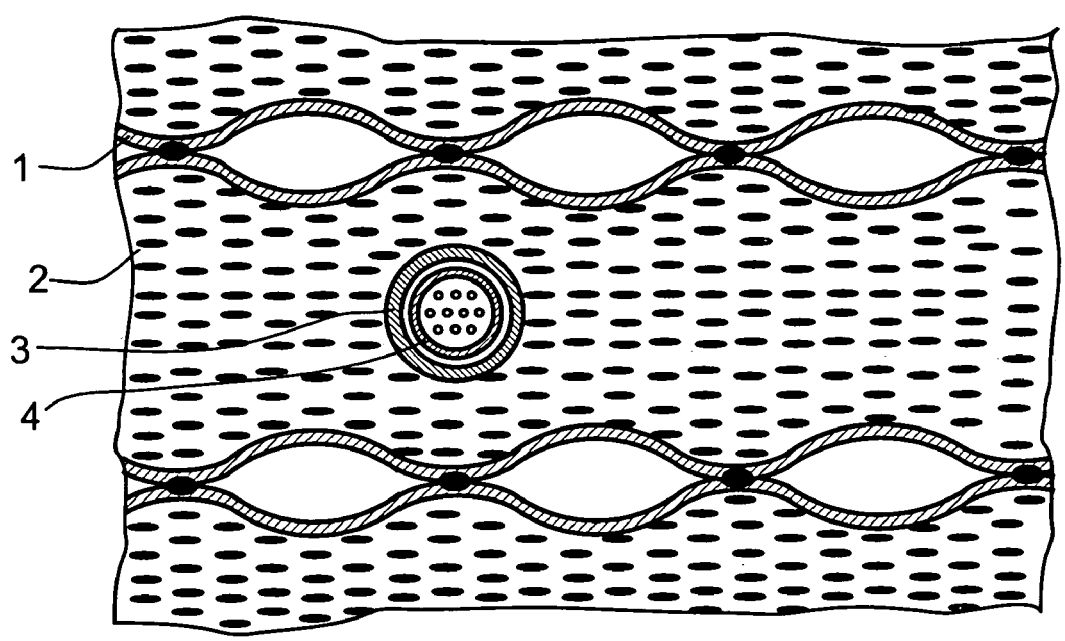
Figure 2:
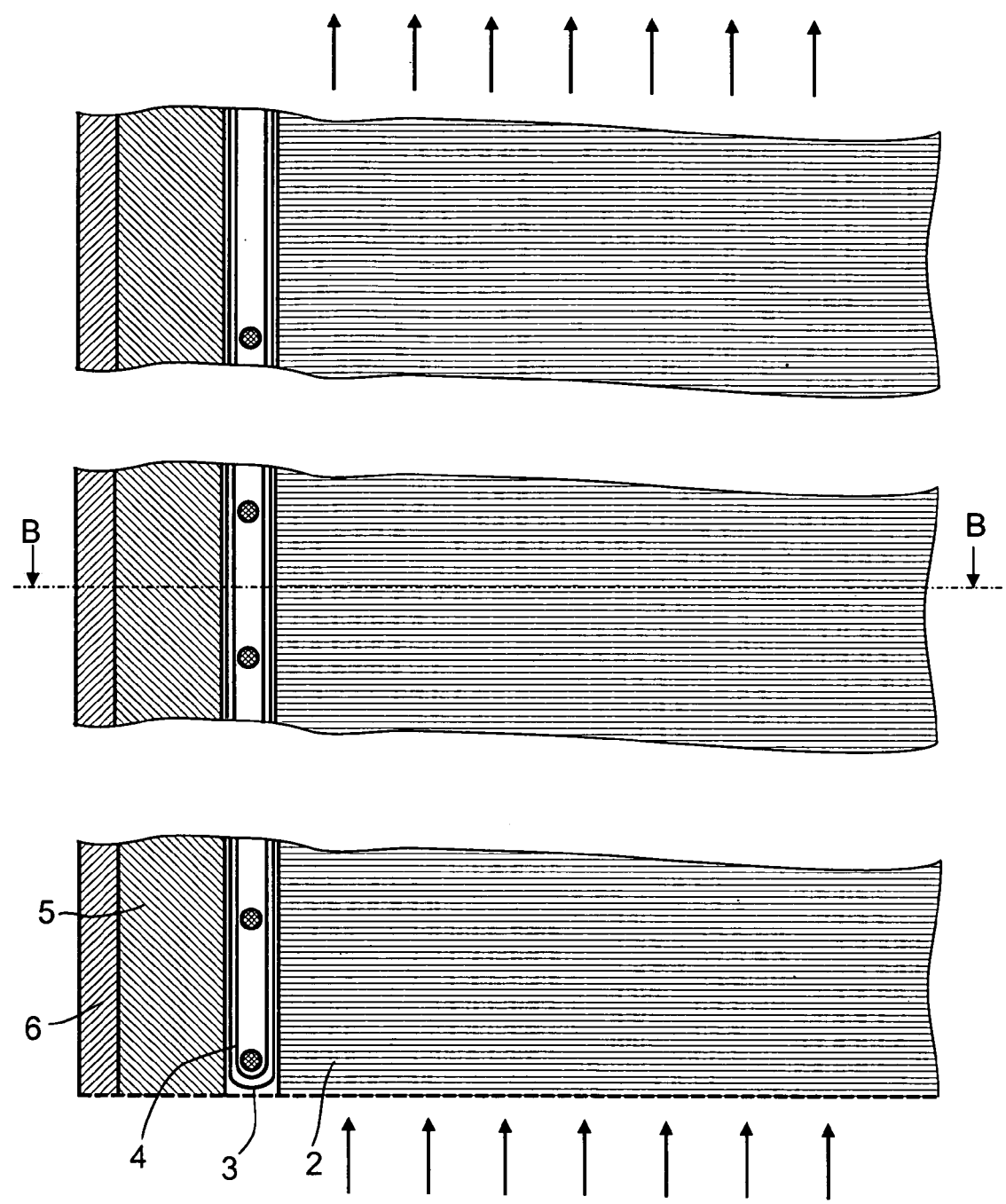
Figure 2A:
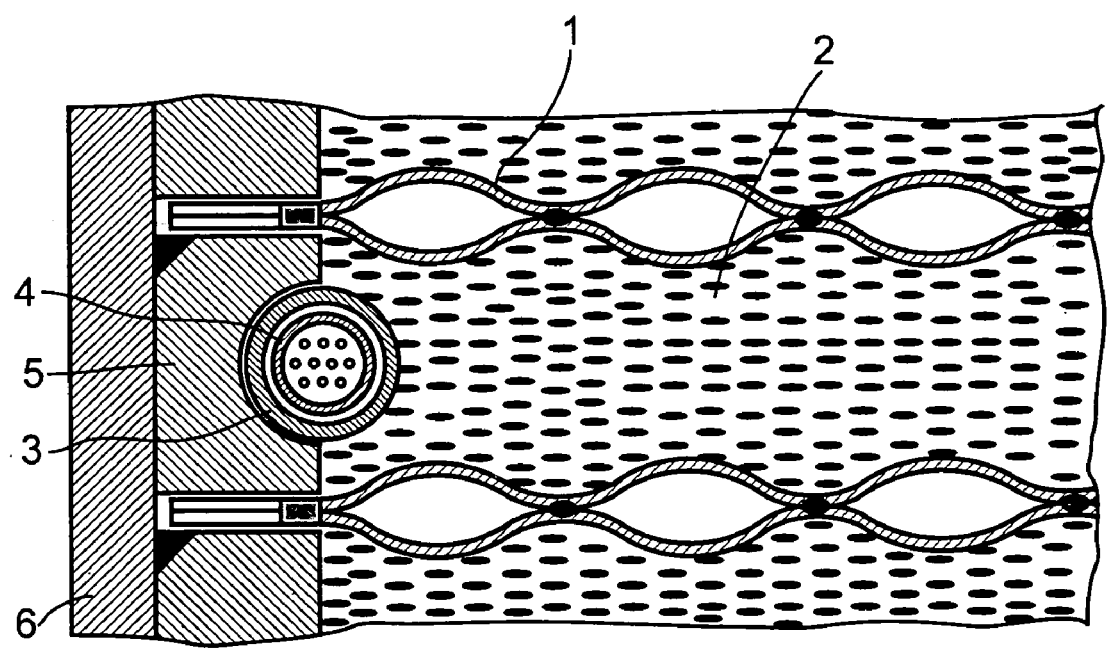
Figure 3:
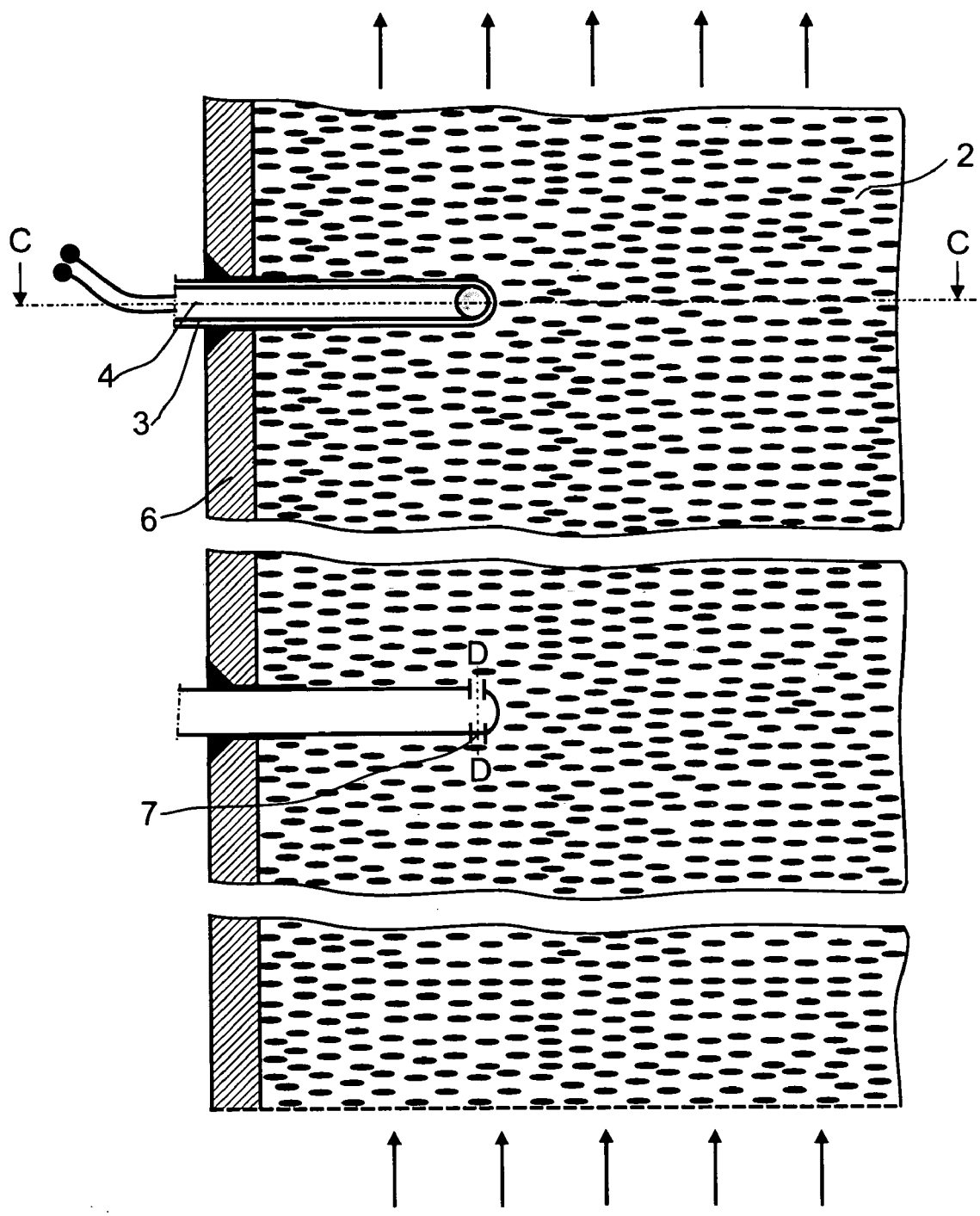
Figure 3A:
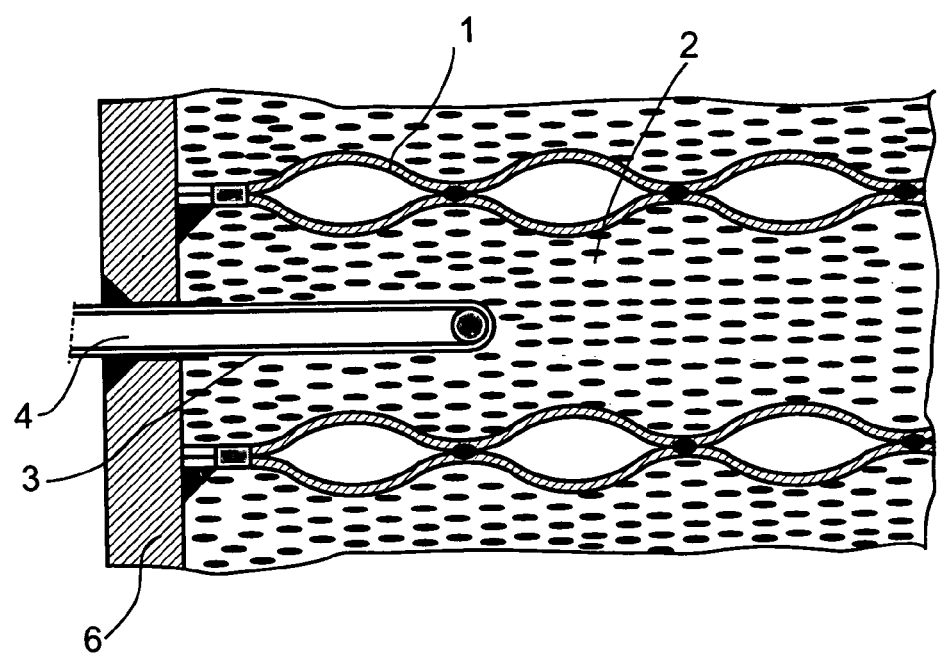
Figure 3B:
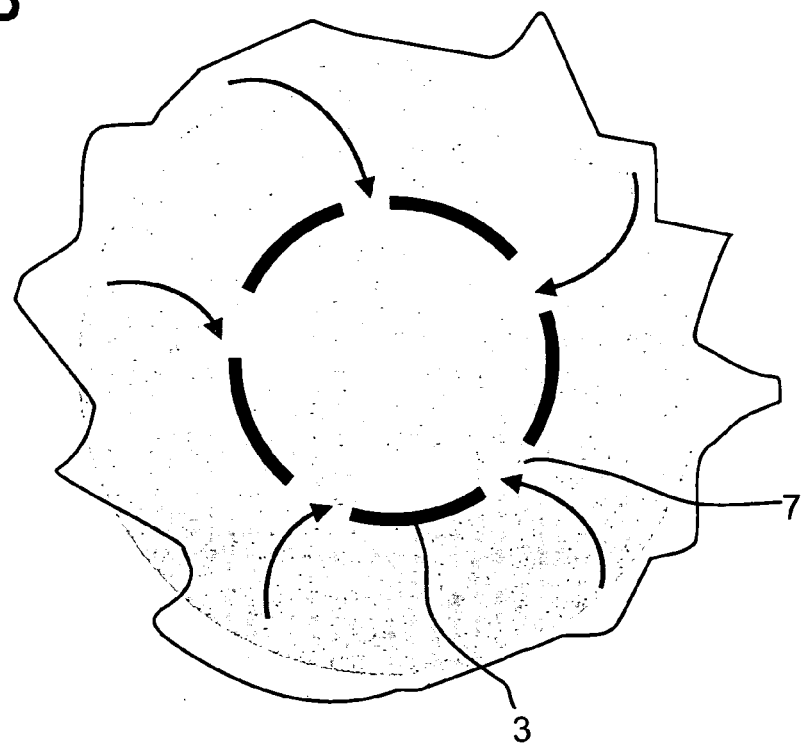
Figure 4A:
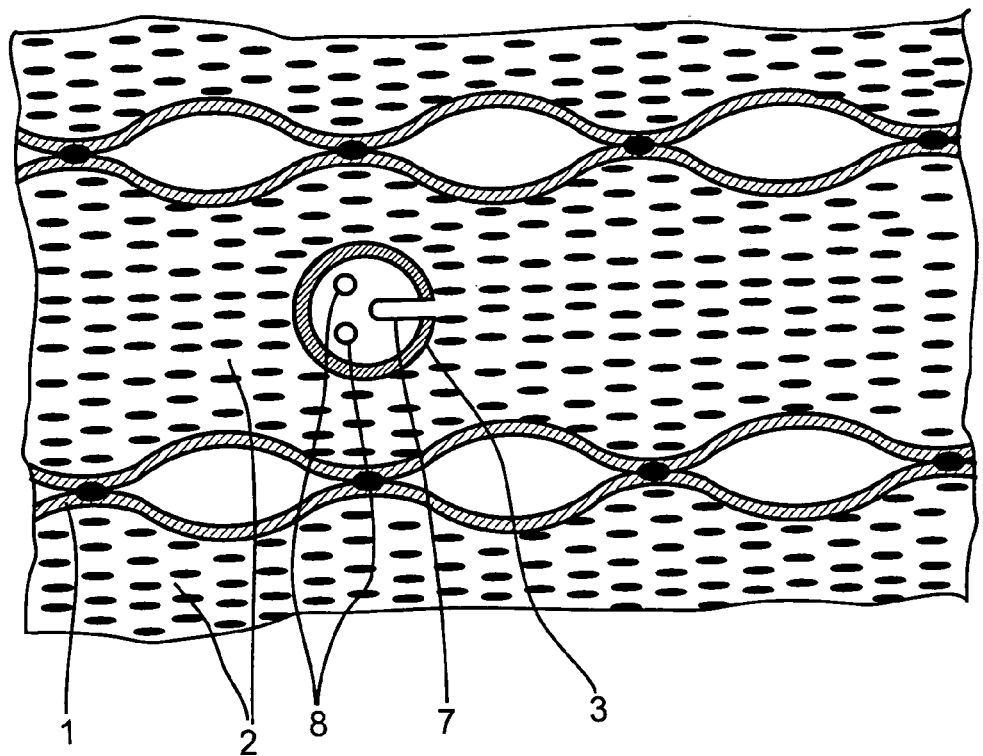
Figure 4:
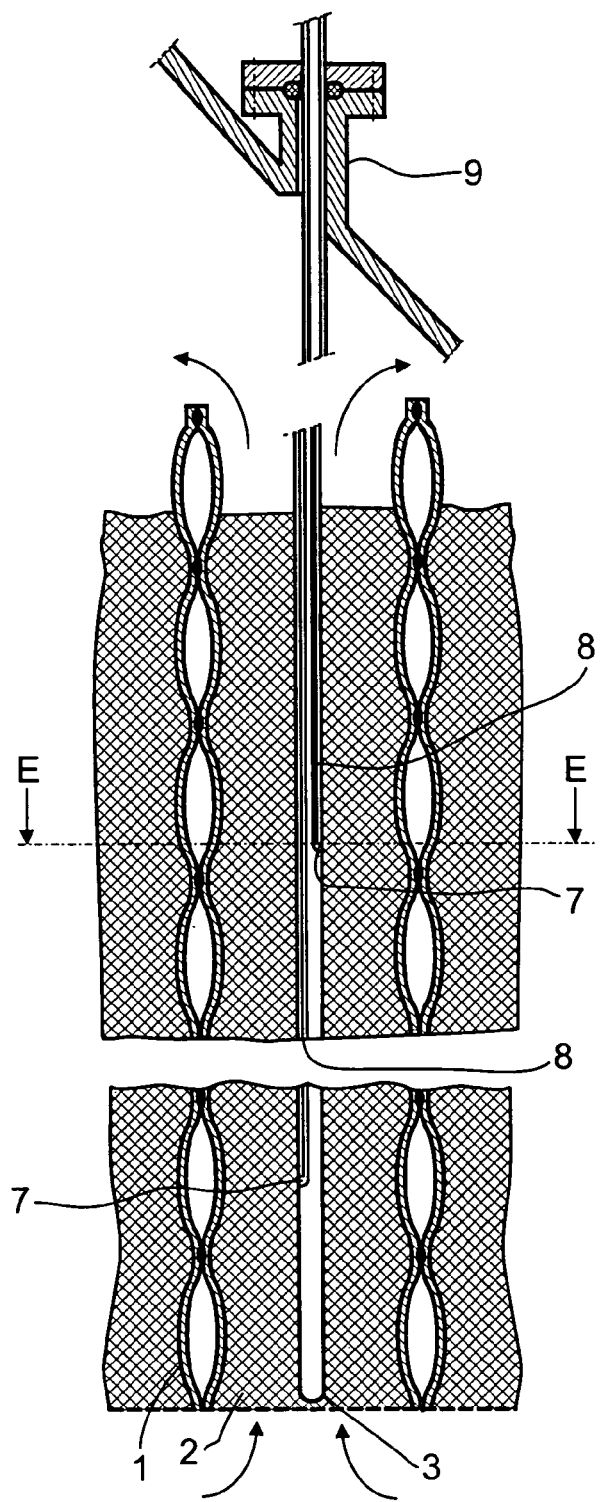
Figure 5:
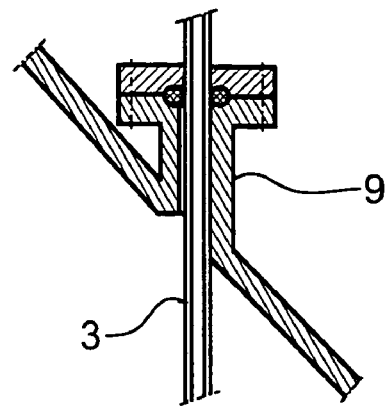
Figure 5:
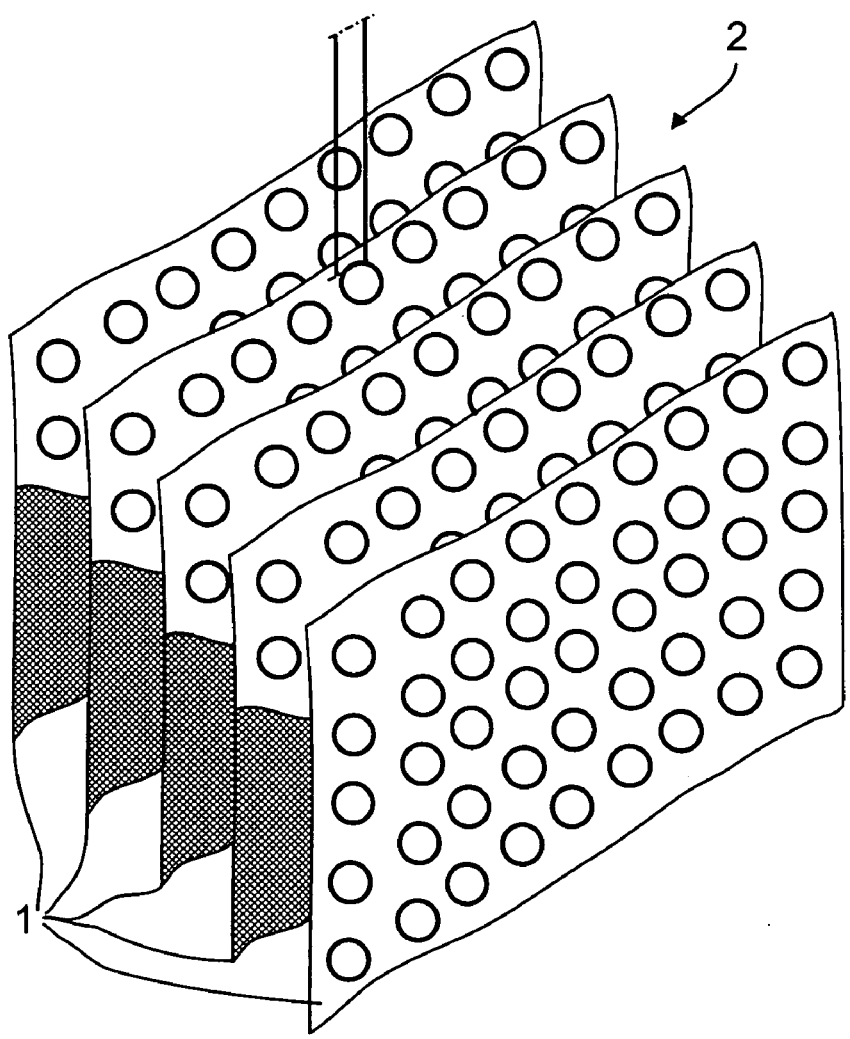

The individual figures show:

FIG. 1 a section from a reactor having thermoplates having a centrally disposed sleeve for accommodating a thermoelement, in longitudinal section, with cross-sectional illustration in FIG. 1A, FIG. 2 a section through a further embodiment with sleeve disposed laterally, in longitudinal section, with cross-sectional illustration in FIG. 2A, FIG. 3 a further embodiment with sleeve disposed horizontally in the gap, in longitudinal section, with cross-sectional illustration in FIG. 3A and detail illustration in FIG. 3B, FIG. 4 a section from a further embodiment with a sleeve having perforations and sampling tube, in longitudinal section, with cross-sectional illustration in FIG. 4A and FIG. 5 the schematic illustration for the installation of an inventive sleeve in a thermoplate module.

Figure 6:
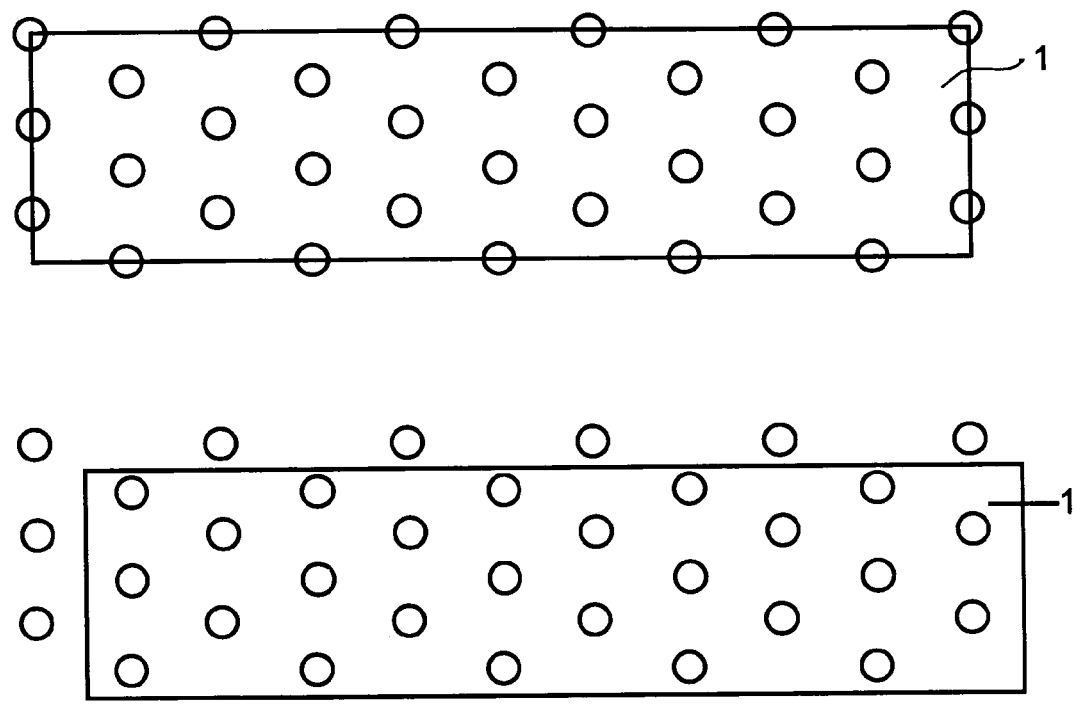

FIG. 6 a schematic of preferred weld point distributions on the surface of thermoplates.

In the figures, identical reference numerals denote identical or corresponding features.

FIG. 1 shows a schematic of a section from a reactor having thermoplates 1 with intermediate gap 2 into which the fixed catalyst bed has been introduced. In the preferred embodiment shown, a sleeve 3 is disposed centrally in the gap 2 and encloses a thermoelement 4 which, by way of example, has 4 measurement points. The sleeve 3 and the thermoelement 4 project out of the reactor through a nozzle in the reactor jacket.

The cross-sectional illustration in FIG. 1A illustrates the cylindrical geometry of the sleeve 3 with thermoelement 4 disposed therein.

The schematic illustration in FIG. 2 shows a section from a reactor in longitudinal direction, in the region of a gap 2 between two thermoplates which are not shown. In the gap 2, at the lateral boundary 6 thereof, is disposed a sleeve 3 having thermoelement 4. Between sleeve 3 and lateral boundary of the gap 2 is provided an insulation element 5.

The cross-sectional illustration in FIG. 2 illustrates the thermoplates 1, including their securing to the lateral boundary 6, and also the cylindrical design of the sleeve 3 with thermoelement 4 and form-fitting design of the insulation element 5.

FIG. 3 shows a schematic of a section from a further embodiment with horizontal arrangement of a sleeve 3 with thermoelement 4 in a gap 2. In the vicinity of its end projecting into the gap, the sleeve has perforations 7, through which samples of the reaction mixture can be taken.

The schematic illustration in FIG. 4 shows a longitudinal section through a further embodiment having a sleeve 3 with perforations 7 in the sleeve 3 to take samples into the sampling tubes 8. The sleeves 3 with sampling tubes 8 project out of the reactor through the nozzle 9.

The cross-sectional illustration in FIG. 4A illustrates the embodiment of the sleeve 3 in cross section, with orifice 7 and sampling tube 8.

FIG. 5 shows a schematic of a section from a reactor having parallel thermoplates 1 with intermediate gaps 2. By way of example, a sleeve 3 is shown and projects into a gap 2 between two thermoplates 1, in the longitudinal direction thereof, and opens outside the reactor through a nozzle 9 in the reactor jacket.

FIG. 6 shows two preferred weld point distributions on the surface of thermoplates: in each case, a rectangular surface section of a thermoplate 1 corresponding to five times the weld point separation on the horizontal axis and five times the row separation on the vertical axis is shown. The upper illustration in FIG. 6 shows a preferred weld point distribution having a total of 33 weld points on the surface section shown of a thermoplate 1 having five times the weld point separation and five times the row separation, and the lower illustration a further preferred arrangement having 25 weld points on a surface section of the same dimensions.

What is claimed is:

1. A process for preparing (meth)acrolein and/or (meth)acrylic acid by partially oxidizing $C_3$ and/or $C_4$ precursor compounds in the gas phase in the presence of a heterogeneous particulate catalyst, in a reactor having two or more thermoplates arranged vertically and parallel to each other while in each case leaving a gap, the heterogeneous particulate catalyst being installed in the gaps and the gaseous reaction mixture being passed through the gaps, which comprises monitoring, controlling and/or regulating the process by selecting as a monitoring, control and/or regulation parameter one or more temperatures which are measured in one or more gaps, at one or more measurement points which are distributed over the height of each gap.

2. The process according to claim 1, wherein the composition of the gaseous reaction mixture in one or more gaps is selected as a further monitoring, control and/or regulation parameter and is determined at one or more measurement points which are distributed over the height of each gap.

3. The process according to claim 1, wherein the monitoring, control and/or regulation of the process is carried out utilizing an apparatus having a sleeve which is disposed in the gap and opens outside the reactor and in each case encloses one temperature measurement insert having one or more measurement points.

4. The process according to claim 3, wherein the sleeve is disposed in the gap in the longitudinal direction.

5. The process according to claim 3, wherein the thermoplates are disposed in
one or more cuboidal thermoplate modules which are each formed from two or more rectangular thermoplates arranged parallel to each other while in each case leaving a gap,
the thermoplate modules are completely surrounded by a pressure-releasing, predominantly cylindrical shell, comprising a cylinder jacket and hoods which close it at both ends and whose longitudinal axis is aligned parallel to the plane of the thermoplates,
one or more sealing elements are arranged in such a way that the gaseous reaction mixture, apart from flowing through the reactor interiors bounded by the hoods, only flows through the gaps, and
each thermoplate module having one or more mutually independent temperature measurement inserts is equipped preferably with two or three temperature measurement inserts.

6. The process according to claim 3, wherein the temperature measurement insert is a multithermoelement.

7. The process according to claim 3, wherein the sleeve is a metallic tube, having an external diameter in the range from 4 to 15 mm and further having a wall thickness of from 0.8 to 1.5 mm.

8. The process according to claim 3, wherein the sleeve has a disconnection point within the reactor interior.

9. The process according to claim 3, wherein the measurement points of the temperature measurement insert are arranged with a relatively small separation from each other in reactor regions having expected temperature extremes and/or particularly large temperature gradients, and with a relatively large separation from each other in the remaining reactor regions.

10. The process according to claim 3, wherein the temperature measurement insert has from 5 to 60 measurement points.

11. The process according to claim 10, werein the temperature measurement insert has 20 measurement points and an external diameter of about 3.8 mm, and the sleeve has an external diameter of 6 mm or of ¼ inch and an internal diameter of 4 mm or of 5/32 inch.

12. The process according to claim 10, wherein the temperature measurement insert has 40 measurement points and an external diameter of about 2.5 mm, and the sleeve has an external diameter of 5 mm or of 3/16 inch and an internal diameter of 3 mm or of ⅛ inch.

13. The process according to claim 4, wherein the sleeve is disposed in the gap centrally in the longitudinal direction.

14. The process according to claim 4, wherein the sleeve is disposed at the lateral boundary of the gap.

15. The process according to claim 14, wherein an insulation element is provided between the lateral boundary of the gap and the sleeve, the sleeve is installed in the gap in a fixed manner, and the sleeve has a square or semicircular section.

16. The process according to claim 3, wherein the sleeve is disposed horizontally in the gap.

17. The process according to claim 2, which, in addition to the apparatus defined in claim 3, utilizes in each case one sleeve in one or more gaps which has perforations and also at least one sampling tube for introduction into the sleeve, said sampling tube being disposed in the sleeve in such a way that the gaseous reaction mixture flows through the perforations in the sleeve into the sampling tube and is removed from the sampling tube outside the reactor and analyzed.

18. The process according to claim 17, wherein the sampling tube is connected to the sleeve in a fixed manner, in such a way that an orifice of the sampling tube is disposed directly on a perforation of the sleeve.

19. The process according to claim 17, wherein the sampling tube is disposed in the perforated sleeve in a rotatable manner and has two or more orifices disposed over its jacket surface offset in such a way that the gaseous reaction mixture always flows into the sampling tube only through one of the orifices.

20. The process according to claim 19, wherein the orifices of the sampling tube are designed as slots in the longitudinal direction thereof.

21. The process according to claim 17, wherein each sampling tube has two or more, mutually separate chambers, each having an orifice into which the gaseous reaction mixture flows through the perforations in the sleeve, and the gaseous reaction mixture is removed separately from each chamber and analyzed.

22. The process according to claim 21, wherein the chambers are arranged mutually adjacently or concentrically.

23. The process according to claim 20, wherein the sampling tube having a plurality of chambers is designed in a rotatable manner about its longitudinal axis.

24. The process according to claim 17, wherein two or more sampling tubes are provided and are each connected in a fixed manner to the sleeve, in such a way that the orifice of each sampling tube is disposed directly on a perforation of the sleeve, and the individual sampling tubes open in the gap each at a different height.

25. The process according to claim 17, wherein the sleeve is itself designed as a sampling tube.

26. A process for incorporating an apparatus according to claim 3 into a reactor, wherein the apparatus is installed from the same side of the reactor as the feed of the gaseous reaction mixture.

27. The process according to claim 26, wherein the apparatus is installed and the gaseous reaction mixture is fed into the reactor in each case from above, and the sleeve has perforations only in the upper region of the gap.

28. The process according to claim 26, wherein the apparatus is installed and the gaseous reaction mixture is fed into the reactor in each case from below, and a heat carrier is passed through the thermoplates and partially or fully evaporates under reaction conditions.

* * * * *